ns Patent [19]

[11] 4,385,063
[45] May 24, 1983

[54] THIENO [3'2':5,6]CYCLOHEPTA [1,2-B]PYRROLE DERIVATIVES

[75] Inventors: Alexander C. Goudie; Robert W. Ward, both of Harlow; Howard E. Rosenberg, New Barnet, all of England

[73] Assignee: Beecham Group Limited, England

[21] Appl. No.: 240,840

[22] Filed: Mar. 5, 1981

[30] Foreign Application Priority Data

Mar. 6, 1980 [GB] United Kingdom ................ 8007661
Jan. 22, 1981 [GB] United Kingdom ................ 8101982

[51] Int. Cl.³ .................... A61K 31/40; A61K 31/55; C07D 487/04
[52] U.S. Cl. .................................... 424/274; 544/141; 544/146; 548/430; 548/527; 549/76; 549/78
[58] Field of Search .................... 260/326.28; 424/274

[56] References Cited
FOREIGN PATENT DOCUMENTS
2740836 3/1979 Fed. Rep. of Germany .

Primary Examiner—Mary C. Lee

Attorney, Agent, or Firm—Jacobs & Jacobs

[57] ABSTRACT

A compound of formula (I):

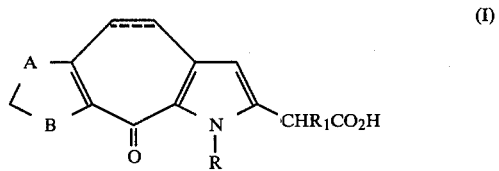

wherein:
R is $C_{1-4}$ alkyl;
$R_1$ is hydrogen or $C_{1-4}$ alkyl;
one of A and B is sulphur, and the other of A and B is carbon doubly bound to the carbon spacing A and B; and
the dotted line represents an optionally present double bond;
and pro-drugs thereof; and pharmaceutically acceptable salts thereof;
have useful anti-inflammatory and analgesic activity.

8 Claims, No Drawings

THIENO [3'2':5,6]CYCLOHEPTA [1,2,-b]PYRROLE DERIVATIVES

This invention relates to novel compounds having anti-inflammatory and analgesic activity, to a process for their preparation, and to pharmaceutical compositions containing them.

Tolmetin, a clinically used anti-inflammatory and analgesic agent of the formula (A):

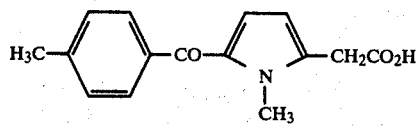

and related compounds have been described in J. Pharmacol. Exp. Therap. 1973, 185, 127–138, U.S. Pat. No. 3,752,826 and U.K. Pat. No. 1,195,628.

A class of compounds also having anti-inflammatory and analgesic activity, but structurally distinct from Tolmetin, has now been discovered. This class of compounds also has a usefully low level of gastric side effects.

Accordingly, the present invention provides a compound of the formula (I):

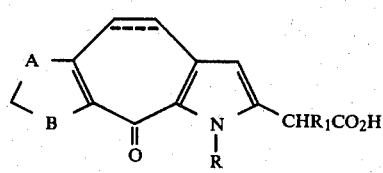

wherein:
R is $C_{1-4}$ alkyl;
$R_1$ is hydrogen or $C_{1-4}$ alkyl;
one of A and B is sulphur, and the other of A and B is carbon doubly bound to the carbon spacing A and B; and
the dotted line represents an optionally present double bond;
and pro-drugs thereof;
and pharmaceutically acceptable salts of the compounds of formula (I) and of their pro-drugs.

Suitably R is methyl or ethyl. Most suitably R is methyl.

Suitably $R_1$ is hydrogen, methyl or ethyl. More suitably $R_1$ is a group $R^1_1$ which is hydrogen or methyl. Most suitably $R_1$ is hydrogen.

Suitably B is the sulphur.

Suitably the dotted line is absent.

Examples of suitable pharmaceutically acceptable salts of the compounds of formula (I) include alkali metal and alkaline earth metal salts such as sodium, potassium, calcium and magnesium salts, and salts of pharmaceutically acceptable nitrogenous bases such as the ammonium salt.

From the aforesaid it will be appreciated that within formula (I) there is a sub-group of compounds of the formula (II):

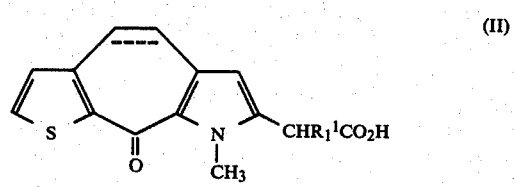

wherein the variables, and suitable values thereof, are as described in relation to formula (I), and pro-drugs, and pharmaceutically acceptable salts.

A second sub-group within formula (I) is of formula (III):

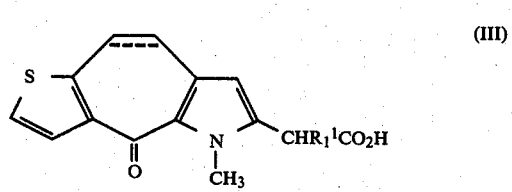

wherein the variables, and suitable values thereof, are as described in relation to formula (I), and pro-drugs, and pharmaceutically acceptable salts.

When used herein the term "pro-drug" means a compound metabolised in vivo to a compound of the formula (I) [or (II) and (III)] or its salt. A pro-drug may be identified by administering the pro-drug to a mammal such as a rat, mouse, monkey, dog or man and identifying the compound of the formula (I) or its salt, for example in blood or urine.

One class of pro-drugs of the compounds of the formula (I) are in vivo hydrolysable esters. Such esters may be simple alkyl esters such as the methyl, ethyl, propyl or butyl esters, simply substituted alkyl esters such as the methoxymethyl, 2-methoxyethyl, 2-hydroxyethyl or benzyl esters or other esters conventionally used in the medical arts as pro-drugs such as a lower acyloxymethyl, α-lower acyloxyethyl, lower alkoxycarbonyloxymethyl, α-lower alkoxycarbonyloxyethyl, phthalidyl or like ester.

A further class of pro-drugs for the compounds of the formula (I) are in vivo hydrolysable amides thereof such as the primary amide, lower alkylamides and di-lower alkylamides thereof.

Another class of pro-drugs for the compounds of the formula (I) are the analogous compounds of lower oxidation state, namely the corresponding compounds in which the $CO_2H$ group is replaced by a CHO or $CH_2OH$ group.

Particularly suitable classes of pro-drugs are those wherein the $CO_2H$ group of the compound of the formula (I), (II) or (III) is replaced by a group of the sub-formulae (a)–(j):

Particularly suitable classes of pro-drugs are those wherein the $CO_2H$ group of the compound of the formula (I), (II) or (III) is replaced by a group of the sub-formulae (a)–(j):

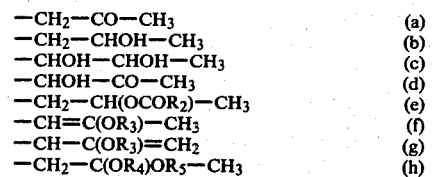

-continued

—CH$_2$—C(OCOR$_6$)=CH$_2$ (i)
—CH=C(OCOR$_6$)—CH$_3$ (j)

wherein R$_2$ is a phenyl, substituted phenyl or C$_{1-4}$ alkyl group optionally substituted by a phenyl or amino group; R$_3$ is a C$_{1-4}$ alkyl group; R$_4$ and R$_5$ are each C$_{1-4}$ alkyl groups or are joined to represent a CH$_2$CH$_2$ or CH$_2$CH$_2$CH$_2$ group; and R$_6$ is a C$_{1-4}$ alkyl group.

Particularly suitable examples of R$_2$ include methyl, ethyl, amino methyl (salted by for example HCl); and phenyl. Preferably R$_2$ is methyl or amino methyl.

Suitable examples of R$_3$, R$_4$ and R$_5$, and R$_6$ include methyl and ethyl, more suitably methyl. R$_4$ and R$_5$ may also be joined as described.

Preferred pro-drugs are those containing sub-formulae (a), (b), (c), (d) and (e) as defined above. Particularly preferred pro-drugs are those containing sub-formula (a) and (e).

In a further aspect this invention provides a pharmaceutical composition which comprises a compound of the formula (I), a pro-drug thereof, or a pharmaceutically salt of the compound of the formula (I) or its pro-drug, and a pharmaceutically acceptable carrier.

The compositions of this invention are useful in treating rheumatic and arthritic conditions because of their anti-inflammatory and analgesic properties. It is believed that their analgesic activity is particularly marked. The compositions may be adapted for administration via the oral, rectal or injection (ie intravenous or intramuscular) routes but since the compositions of this invention do not excessively irritate the gastro-intestinal tract it is preferred that they are adapted for oral administration.

The compositions of this invention may contain diluents, binders, fillers, disintegrants, flavouring agents, colouring agents, lubricants, preservatives or the like in conventional manner. These conventional excipients may be employed in conventional manner, for example as in the preparation of compositions of ketoprofen, indomethacin, naproxen, acetylsalicyclic acid or other anti-inflammatory analgesic agents.

Most suitably the composition of this invention will be in the form of a unit dose such as a tablet, capsule or reconstitutable powder in a sachet. Such unit doses will generally contain from 20 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range 100 to 3000 mg. Alternatively the unit dose may contain from 2-20 mg of a active agent and may be administered in multiples if desired to give the preceeding daily dose.

A favoured form of the composition of this invention is a hard gelatin capsule containing the active agent. The active agent may be in the form of a powder, granulate of the active ingredient in intimate mixture with a lubricant such as magnesium stearate, a filler such as microcrystalline cellulose and a disintegrant such as sodium starch glycollate.

This present invention also provides a method of treating inflammatory and/or painful conditions in mammals which comprises administering an effective amount of a compound of this invention.

Mammals which may be thus treated include humans and domestic animals such as dogs, cats or horses.

The invention also provides a process for the preparation of a compound of the formula (I), which process comprises the basic hydrolysis of an ester of formula (IV):

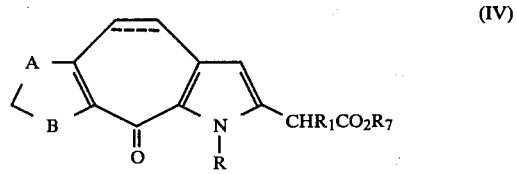

(IV)

wherein R$_7$ is C$_{1-4}$ alkyl, such as ethyl, and thereafter if desired acidifying the resulting salt to form the free acid.

This hydrolysis may be effected by using an hydroxide such as sodium hydroxide in aqueous ethanol.

If desired after this reaction, a R$_1$ is hydrogen compound of the formula (I) may be alkylated to give the corresponding compound wherein R$_1$ is C$_{1-4}$ alkyl. This alkylation may be carried out by reacting the compound of formula (I) wherein R$_1$ is hydrogen with lithium diisopropylamide and an alkyl halide such as methyl iodide.

Alternatively, it may be convenient to alkylate a R$_1$ is H compound of the formula (IV) before the final hydrolysis step. Such alkylations are suitably achieved using sodium hydride and an alkyl halide such as methyl iodide.

The compounds of formula (IV) may themselves be prepared by decarboxylation of a compound of formula (V):

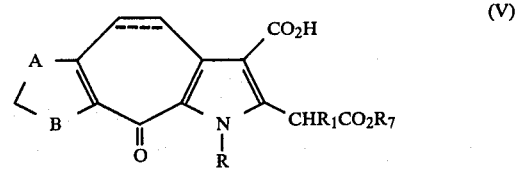

(V)

The decarboxylation may be effected by heating in an inert atmosphere. A decarboxylation aid such as copper/quinoline may be used if necessary.

Compounds of the formula (V) may be prepared by the de-esterification of a compound of formula (VI):

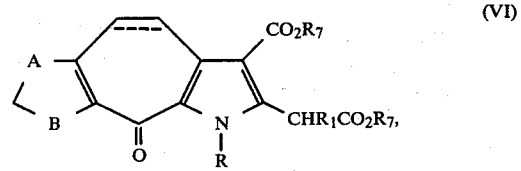

(VI)

and then subsequent selective esterification of the lower chain acid function.

These reactions may be carried out in conventional manner, for example as illustrated in the following Examples.

Compounds of the formula (VI) may themselves be prepared by the cyclisation of a compound of formula (VII):

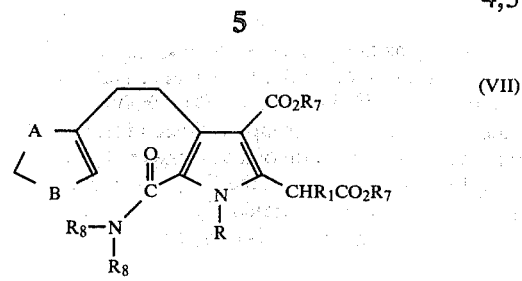

(VII)

wherein $R_8$ is $C_{1-4}$ alkyl (such as methyl), or $NR_8R_8$ represents morpholino, and subsequent oxidation of the thus formed compound, if required, to produce a double bond in the seven membered ring.

Preferably $NR_8R_8$ represents morpholino in formula (VII).

The cyclisation may be carried out, for example, with phosphoryl chloride. The optional oxidation may be carried out in any suitable manner, for example using N-bromosuccinimide in a solvent such as carbon tetrachloride. It will be appreciated that this reaction may only proceed as far as the monobromo or dibromo derivative, in which case further reaction with a base (such as sodium methoxide) or zinc in methanol, respectively, may be necessary.

The compounds of formula (VII) may themselves be prepared by reacting a compound of formula (VIII):

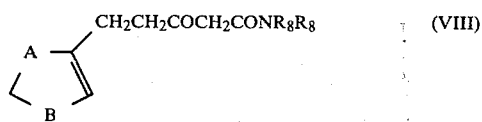

(VIII)

in the Knorr pyrrole synthesis. This reaction is suitably carried out with sodium nitrite, diethyl acetone-1,3-dicarboxylate and zinc.

It will be appreciated that after this pyrrole synthesis, it will be necessary to alkylate the pyrrole nitrogen. This alkylation is suitably carried out using a reagent such as a dialkyl sulphate.

It will also be appreciated that these reactions yield a compound of formula (VII) wherein $R_1$ is hydrogen. If a compound of formula (VII) wherein $R_1$ is alkyl is required, this may readily be prepared by alkylation of the corresponding $R_1$ is hydrogen compound. Suitably this alkylation may be carried out using sodium hydride and an alkyl halide such as methyl iodide.

The compound of formula (VIII) may itself be prepared from halo-, preferably chloro-, methylthiophene and N,N-dialkyl (preferably dimethyl) acetoacetamide or 4-[1,3-dioxobutanyl]morpholine.

The salts of the compounds of the formula (I) may be prepared from the free acids of the formula (I) in any of the conventional ways used to convert an acid to its salt.

The pro-drugs of the compounds of the formula (I) may either be prepared from the compounds of formula (I), or may be synthesised "independently", as appropriate.

All such processes of course form part of this invention.

Examples of preparation of pro-drugs from compounds of the formula (I) include esterification and amidation.

Examples of "independent" synthesis include the preparation of alkyl esters by omitting the final de-esterification stage of the hereinbefore described synthetic procedure for the compound of formula (I).

A compound of the formula (I) wherein the $CO_2H$ group is replaced by a $CH_2COCH_3$ group (i.e. sub-formula (a)) may be prepared by the oxidation of a compound of the formula (IX):

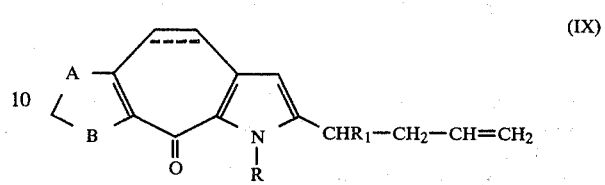

(IX)

This oxidation may be carried out in any convenient manner for example, with oxygen in aqueous dimethylformamide in the presence of palladium chloride and cuprous chloride. This oxidation reaction may be effected using pure oxygen or air. In general it is sufficient to blow air through the reaction mixture at an ambient or slightly elevated temperature to effect oxidation. The desired compound may be obtained from the reaction mixture by dilution with water followed by extraction into water-immiscible solvent such as chloroform which may then be dried and evaporated. This initial crude material may be purified chromatographically if desired, for example by column chromatography over silica gel using 1:1 ether:petrol eluant.

The compounds of the formula (IX) may be prepared by the decarboxylation of a corresponding compound of the formula (X):

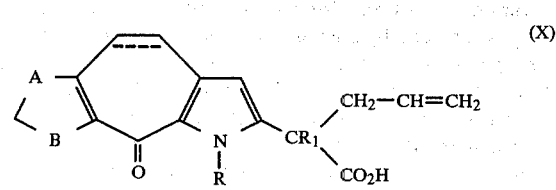

(X)

The decarboxylation may be effected by heating, for example to 170°–210° C. The desired product may be obtained by trituration under a non-hydroxylic solvent such as chloroform.

The acid of the formula (X) may be obtained by hydrolysis of the corresponding $C_{1-4}$ alkyl ester such as the ethyl ester using normal sodium hydroxide solution followed by neutralisation with hydrochloric acid. This $C_{1-4}$ alkyl ester may be prepared by the allylation of the corresponding compound of the formula (IV). Such allylations may be brought about by generating an anion of the formula (IV), for example with sodium hydride in dimethoxyethane, and quenching the said anion with allyl bromide.

Alternatively, compounds of the formula (X) may be prepared by the direct allylation of a compound of formula (I), with for example allyl bromide in the presence of lithium diisopropylamide.

The pro-drugs of compounds of the formula (I) wherein the $CO_2H$ group is replaced by a $CH_2COCH_3$ group may also be prepared by thermal decomposition of a compound of formula (XI):

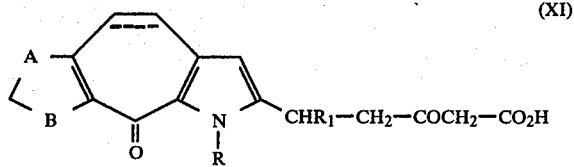

(XI)

This decomposition may suitably be carried out with or without an inert solvent, such as dimethyl sulphoxide, at about 60° to 100° C.

The intermediates of formula (XI) may themselves be prepared from a compound of formula (XII):

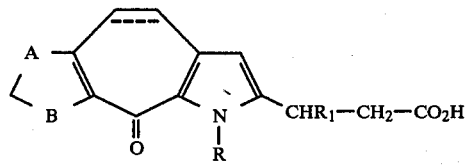

(XII)

via a suitably activated derivative such as the ethoxycarbonyl derivative, for example following the general method described in Synthesis 1979, p. 787.

It will be appreciated that the compounds of formula (XII) may be prepared in analogous manner to the preparation of the corresponding compounds of formula (I), except that dimethyl 3-oxoadipate is suitably used in the Knorr pyrrole synthesis reaction. Also, in such a synthesis, it will be appreciated that there is no need to protect the lower chain carboxyl function prior to the decarboxylation step (see Example 2 (g)).

Compounds of the formula (I) wherein the $CO_2H$ group is replaced by a group of the sub-formula (b) may be prepared by the reduction of a corresponding compound of the formula (I) wherein the $CO_2H$ group is replaced by a group of the sub-formula (a). Such a reduction may use a complex hydride such as sodium borohydride. Mild conditions and avoidance of excess reagent prevent reduction of the aromatic carbonyl. The desired compound may be purified by conventional methods of column chromatography.

Pro-drugs of the compounds of the formula (I) containing a group of the sub-formulae (e), (f), (g), (h), (i) and (j) may be prepared, for example, as described in Belgian Pat. No. 866,857 (U.S. Pat. No. 4,200,645).

Thus compounds of the formula (II) wherein the $CO_2H$ group is replaced by the sub-formula (e) may be prepared by the acylation of a corresponding compound containing the sub-formula (b). Suitable methods of acylation include those described in Belgian Pat. No. 854,429 (U.K. Pat. No. 1,538,473).

Compounds of the formula (II) wherein the $CO_2H$ group is replaced by sub-formula (f) or (j); (g) or (i); or (h); may be prepared by the enol acylation, enol etherification or acetalation of a corresponding compound containing the sub-formula (a). Suitable methods of enol acylation, enol etherification and acetalation include those described in Offenlegungsschrift No. P 26 47 966.3 (U.S. Pat. No. 4,180,585).

Compounds of the formula (I) wherein the $CO_2H$ group is replaced by a group of the sub-formula (d) may be prepared by the reaction of m-chloroperbenzoic acid and a compound of the formula (I) in which the $CO_2H$ group is replaced by a group of the sub-formula (f).

Such reactions are generally carried out at 0°–5° C. in mixed solvents such as diethyl ether/water.

Compounds of the formula (I) wherein the $CO_2H$ group is replaced by a group of the sub-formula (c) may be prepared by reduction of a corresponding compound of the formula (I) in which the $CO_2H$ group is replaced by a group of the sub-formula (d). Such a reaction may be effected using sodium borohydride under conventional conditions.

Salts of pro-drugs, when appropriate, may be prepared in conventional manner.

The novel intermediates in the hereinbefore described preparative processes, such as compounds of formulae (IV), (V), (VI), (VII), (VIII), (IX), (X), (XI) and (XII), form part of the invention.

Some of the compounds of the formula (I) may form hydrates, and of course such hydrates are included within the scope of this invention.

It will be appreciated the compounds of the formula (I) wherein $R_1$ is alkyl (and pro-drugs and pharmaceutically acceptable salts thereof) have an asymmetric centre. The present invention of course extends to the enantiomers thereof, and to the racemates of these enantiomers. The enantiomers may be resolved from their racemates by conventional resolution techniques.

An alternative reaction for the preparation of a compound of the formula (VI) as hereinbefore comprises the cyclisation of a compound of formula (XIII):

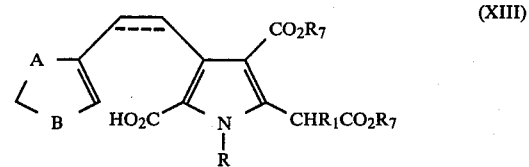

(XIII)

This cyclisation reaction is suitably carried out by a Friedel-Crafts reaction, using a Lewis acid such as $AlCl_3$ or $SnCl_4$ and the acid of formula (XIII) in the form of its acid chloride or mixed anhydride.

Compounds of the formula (XIII) may themselves be prepared by reacting a compound of formula (XV):

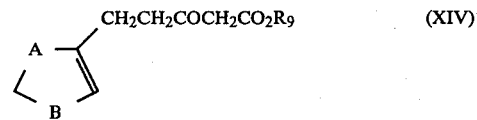

(XIV)

wherein $R_9$ is a readily hydrolysable or hydrogenolysable ester, in a Knorr synthesis; and subsequently, alkylating the pyrrole N-hydrogen; and then converting the $R_9$ group to hydrogen.

The Knorr pyrrole synthesis is suitably carried out with sodium nitrite, diethyl acetone-1,3-dicarboxylate and zinc, in acetic acid.

The N-H alkylation may suitably be carried out with $K_2CO_3$ and a dialkyl sulphate such as dimethyl sulphate.

The $R_8$ group, which is suitably benzyl, may be removed by hydrolysis or hydrogenolysis.

In the cyclisation reaction of a compound of formula (XIII), it is not necessary that the pyrrole N substituent is alkyl. In other words, after the pyrrole synthesis reaction on the compound of the formula (XIV), the pyrrole N-hydrogen need not be alkylated.

In such circumstances, following the reaction procedure described above for converting a compound of the formula (VI) into a compound of formula (I), but with a compound of formula (VI) wherein the pyrrole N substituent is hydrogen, not alkyl, leads to a compound of formula (I)':

(I)'

Thus, an alternative process according to the invention comprises the alkylation of a compound of the formula (I)'; to give a compound of the formula (I).

This alkylation may suitably be carried out using for example a dialkyl sulphate.

After this reaction, optional reactions as hereinbefore described may be carried out.

It should perhaps be noted that this process is not believed to be particularly advantageous.

For the sake of completeness, it is pointed out that appropriate pro-drugs of the formula (I) may be prepared by a process entailing as the final step the alkylation of the corresponding pyrrole N-hydrogen pro-drug. Such pyrrole N-hydrogen pro-drugs may be prepared in analogous manner to the preparation of the corresponding pyrrole N-alkyl pro-drugs.

Novel intermediates of formulae (XIII), (XIV) and (I)' form an important aspect of this invention, as do novel intermediates of formulae (IV)', (V)' and (VI)' which are as defined in formulae (IV), (V) and (VI) but with the pyrrole N-substituent being hydrogen.

Pro-drugs of the compounds of the formula (I) wherein the $CO_2H$ group is replaced by sub-formula (a) $CH_2COCH_3$ can be prepared from the corresponding pro-drugs having sub-formula (g) $CH—C(OR_3)=CH_2$, for example by stirring in dilute acid.

A further process for the preparation of a pro-drug of formula (g) is the decarboxylation of a compound of formula (X)':

(X)'

This decarboxylation conveniently proceeds in one step to give pro-drugs of the compounds of formula (I) wherein the $CO_2H$ group is replaced by sub-formula (a) $CH_2COCH_3$.

Compounds of formula (X)', which are novel intermediates and as such form an important part of this invention, may be prepared by the alkoxyallylation of a compound of formula (I) or (IV), suitably for example with 2-methoxyallylbromide. These reactions, and the decarboxylation of compounds of formula (X)', suitably are carried out in analogous manner to the preparation and decarboxylation of a compound of formula (X) as hereinbefore described.

The following Examples illustrate the invention.

EXAMPLE 1

(a) N,N-Dimethyl-3-oxo-5-(3-thienyl)-pentanamide $CH_2CH_2COCH_2CONMe_2$

N,N-Dimethyl acetoacetamide (46.8 g; 0.363 mole) was converted to its dianion by treatment with 80% sodium hydride (11.8 g; 0.393 mole) in dry tetrahydrofuran (350 ml) under nitrogen, at 20° C. The resulting suspension was diluted with dry ether (1 L) and stirred mechanically for 15 minutes at 0° C. before a solution of n-butyl lithium in hexane (227 ml; 1.6 M; 0.363 mole) was added dropwise. To the now clear mixture was then added 3-chloromethyl thiophene (38 g; 0.287 mole) in dry tetrahydrofuran (50 ml), again dropwise, and the reaction allowed to warm up to room temperature. After the solution had stood at room temperature overnight the solvents were removed on a rotary evaporator and the residue acidified with dilute HCl in the presence of ethyl acetate (200 ml). The organic layer was separated off and the aqueous layer extracted once again with ethyl acetate (200 ml). The combined organic layers were dried (anhydrous $MgSO_4$), and evaporated to give an oil which was purified on a short silica gel column using chloroform as eluant affording the product as a red-brown oil (48.5 g; 75%).

N.M.R. δ ($CDCl_3$:
  7.15 (1H, m);
  6.88 (2H, m);
  3.5 (2H, s);
  2.9 (10H, m).

(b) Ethyl 5-N,N-dimethylcarboxamide-4-[2-(3-thienyl)-ethyl]-3-ethoxycarbonyl-pyrrole-2-acetate A solution of sodium nitrite (14.8 g) in water (23.5 ml), was added dropwise to a stirred solution of N,N-dimethyl-3-oxo-5-(3-thienyl)-pentanamide (48.5 g) in glacial acetic acid (400 ml), cooled to below 10° C. When the addition was complete the mixture was stirred for 3 hours at room temperature and then left to stand overnight before adding to a mechanically stirred solution of diethyl acetone-1, 3-dicarboxylate (43.7 g) in glacial acetic acid (200 ml) heated to 70°. Zinc powder (50.7 g) and anhydrous sodium acetate (57.3 g) were added concurrently to the above mixture such that the temperature was maintained in the range 75°–80° C. After these additions the mixture was refluxed for 1 hour before pouring into water (1.5 l) to give a grey solid which was filtered off, dried and recrystallised from toluene to afford a white solid (38.5 g; 47%), m.p. 139°–142° C.

N.M.R. δ ($CDCl_3$):
  10.33 (1H, broad s);

7.15 (1H, m);
6.88 (2H, m);
4.26 (2H, q, J=7 Hz);
4.13 (2H, q, J=7 Hz);
3.96 (2H, s);
2.95 (10H, broad s);
1.3 (3H, t, J=7 Hz);
1.23 (3H, t, J=7 Hz).

(c) Ethyl 5-N,N-dimethylcarboxamido-4-[2-(3-thienyl)-ethyl]-3-ethoxycarbonyl-1-methylpyrrole-2-acetate

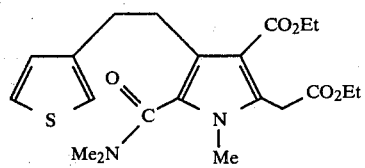

The NH pyrrole (38 g) was suspended in isobutyl methylketone (650 ml) and anhydrous potassium carbonate (15.5 g) added. Dimethyl sulphate (9.8 ml) was added to the magnetically stirred mixture and the reaction brought to reflux temperature. After overnight reflux the reaction was examined by t.l.c. (2% MeOH/CHCl$_3$/Silica) and another batch of potassium carbonate and dimethyl sulphate added. This procedure was repeated at intervals until all the NH pyrrole had reacted (by t.l.c.). The reaction was then cooled, poured into water, the organic layer separated and the aqueous layer extracted with ethyl acetate (1×200 ml). The combined organic layers were washed with water (2×500 ml), dried (anhydrous MgSO$_4$), filtered and evaporated to give the crude product (38 g) as an oil.
N.M.R. δ (CDCl$_3$)
7.15 (1H, m);
6.88 (2H, m);
4.26 (2H, q, J=7 Hz);
4.13 (2H, q, J=7 Hz);
3.96 (2H, s);
3.43 (3H, s);
2.95 (10H, broad s);
1.3 (3H, t, J=7 Hz);
1.23 (3H, t, J=7 Hz).

(d) Diethyl 4,5-dihydro-8-methyl-9-oxo-9H-thieno[3',2':5,6]cyclohepta[1,2-b]pyrrole-7-acetate-6-carboxylate

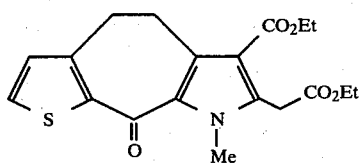

The crude NMe pyrrole (38 g) was dissolved in phosphoryl chloride (200 ml), under an atmosphere of nitrogen and the stirred mixture refluxed overnight. After cooling the reaction was poured carefully onto ice covered with ethyl acetate. Neutralization of the aqueous solution was achieved by the addition of solid sodium carbonate. The organic layer was separated and the aqueous layer extracted with ethyl acetate (1×500 ml). The combined organic layers were washed with saturated sodium chloride solution (2×150 ml), water (1×150 ml), dried (anhydrous MgSO$_4$), filtered and evaporated to give a black oil. Purification by column chromatography, eluting with chloroform on silica gel, afforded the product as a solid, m.p. 103°-105°.
N.M.R. δ (CDCl$_3$):
7.46 (1H, d, J=5 Hz);
6.9 (1H, d, J=5 Hz);
4.3 (2H, q, J=7 Hz);
4.16 (2H, q, J=7 Hz);
4.1 (2H, s);
3.9 (3H, s);
3.56-3.23 (2H, m);
3.13-2.83 (2H, m);
1.33 (3H, t, J=7 Hz);
1.26 (3H, t, J=7 Hz).

(e) 4,5-Dihydro-8-methyl-9-oxo-9H-thieno[3',2':5,6]cyclohepta[1,2-b]pyrrole-7-acetic acid-6-carboxylic acid

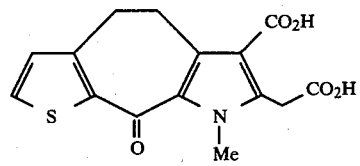

The above diethyl ester (4.6 g) in ethanol (10 ml) was refluxed with 25% NaOH (60 ml) for 2 hour, left to stand overnight and then poured into water. The aqueous solution was washed with ether (1×75 ml), acidified and the resulting solid filtered off and dried (3.9 g, 100%), m.p. 194°-196° (recrystallised from ethanol/water).

(f) Ethyl 4,5-dihydro-8-methyl-9-oxo-9H-thieno[3',2':5,6]cyclohepta[1,2-b]pyrrole-7-acetate-6-carboxylic acid

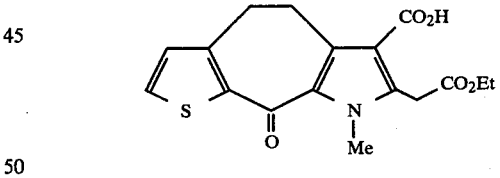

A suspension of the above acid (3.9 g) was refluxed with 0.5% ethanolic HCl (86 ml) for 1 hour to give a clear solution. On cooling a precipitate appeared which was isolated to give the required product, (3.48 g, 82%), m.p. 191°-194°.
N.M.R. δ (CDCl$_3$/C$_5$D$_5$N):
8.33 (1H, broad s);
7.43 (1H, d, J=5 Hz);
6.86 (1H, d, J=5 Hz);
4.29 (2H, s);
4.16 (2H, q, J=7 Hz);
3.91 (3H, s);
3.66-3.33 (2H, m);
3.13-2.8 (2H, m);
1.23 (3H, q, J=7 Hz).

(g) Ethyl 4,5-8-methyl-9-oxo-9H-thieno[3',2':5,6]cyclohepta[1,2-b]pyrrole-7-acetate

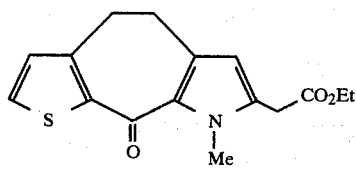

The above acid (3.48 g) was heated under nitrogen at 218° in an oil bath for 1¾ hours. Evolution of gas was observed. The reaction was cooled, suspended in ethyl acetate and the organic layer washed with dilute sodium hydroxide (1×75 ml), water (1×75 ml), dried (anhydrous MgSO₄), filtered and evaporated to give an oily-solid (2.2 g). Purification by column chromatography using silica gel and elution with chloroform afforded the product as a solid (1.8 g; 60%), m.p. 87.5°–88.5° (pet.ether 60°–80°).

N.M.R. $\delta$ (CDCl₃):
7.35 (1H, d, J=5 Hz);
6.82 (1H, d, J=5 Hz);
5.93 (1H, s);
4.15 (2H, q, J=7 Hz);
3.88 (3H, s);
3.62 (2H, s);
2.92 (4H, s);
1.26 (3H, q, J=7 Hz).

A repetition of this reaction on a larger scale, using pentane as recrystallization solvent, gave a product of m.p. 90°–91° C., having the same NMR as above.

(h) 4,5-Dihydro-8-methyl-9-oxo-9H-thieno[3',2':5,6]cyclohepta[1,2-b]pyrrole-7-acetic acid

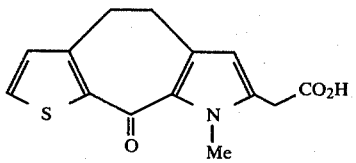

The above ester (1.6 g) in ethanol (10 ml) was added to 5% sodium hydroxide solution (100 ml) and the mixture refluxed for 2 hours. The resulting solution was cooled, diluted with water (100 ml) washed with ethyl acetate (2×75 ml) and acidified. On cooling crystals appeared and the product was isolated by filtration. Recrystallisation from chloroform/hexane afforded the product as a solid (0.58 g, 32%), m.p. 155°–7° (decarboxylation).

N.M.R. $\delta$ (CDCl₃):
10.13 (1H, broad s);
7.45 (1H, d, J=5 Hz);
6.9 (1H, d, J=5 Hz);
6.0 (1H, s);
3.9 (3H, s);
3.7 (2H, s);
2.93 (4H, s).

Observed M⁺ = 275.0629.

The above reaction was repeated using 9.2 g of the ester and 200 ml sodium hydroxide. After the acidification, the mixture was extracted with CHCl₃ (2×250 ml), the organic layers combined, washed with water, dried (anhydrous Na₂SO₄), filtered and evaporated to give a solid. Recrystallization from chloroform/pentane yielded a solid (8.0 g, 97%), m.p. 157°–158° (decarboxylation), having the same NMR as above.

ALTERNATIVE SYNTHESIS OF COMPOUND OF EXAMPLE 1(d)

(i) 4-[1,3-Dioxo-5-(3-thienyl)-pentyl]morpholine

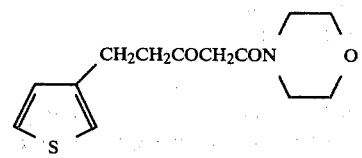

4-[1,3-Dioxobutyl]morpholine[1] (275 g, 1.6 mole) was converted to its dianion by treatment with 50% sodium hydride (77 g, 1.6 moles) in dry tetrahydrofuran (2 l) under nitrogen, at 20° C. The resulting suspension was diluted with dry ether (1 l) and dry tetrahydrofuran (1 l) and stirred mechanically for 30 minutes at 0° C. before a solution of n-butyl lithium in hexane (1000 ml; 1.6 M) was added dropwise. To the now clear mixture was then added 3-bromomethyl thiophene (209 g, 1.2 mole) in dry tetrahydrofuran(250 ml), again dropwise, and the reaction allowed to warm up to room temperature. After the solution had stood at room temperature overnight the precipitate was filtered off, the solvents removed from the filtrate on a rotary evaporator and the residue acidified carefully with dilute hydrochloric acid in the presence of ethyl acetate. The organic layer was separated off and the aqueous layer re-extracted twice more with ethylacetate. The combined organic layers were washed with water, dried (anhydrous MgSO₄), and evaporated to give an oil which was crystallized from dichloromethane/ether after treating with activated charcoal to give a solid (126 g, 39%), m.p. 81°–84° C.

N.M.R. $\delta$ (CDCl₃):
7.25 (1H, m);
7.0 (2H, m);
3.7–3.2 (10H, m);
2.95 (4H, s).

[1] K. Schank, Chem. Ber., 1967, 100, 2292.

(j) 4-(Diethyl-4-[2-(3-thienyl)-ethyl]-pyrrole-2-acetate-3-carboxylate-5-carboxylic acid)morpholide

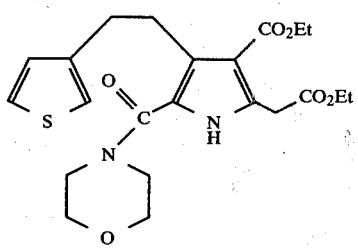

This compound was prepared in an analogous manner to the preparation of ethyl 5-N,N-dimethylcarboxyamido-4-[2-(3-thienyl)-ethyl]-3-ethoxycarbonyl-pyrrole-2-acetate (Example 1(b)), as a solid (yield 58%), m.p. 118°–120° C.

N.M.R. $\delta$ (CDCl₃):

10.1 (1H, broad s);
7.1 (1H, m);
6.83 (2H, m);
4.25 (2H, q, J=7 Hz);
4.14 (2H, q, J=7 Hz);
3.98 (2H, s);
3.56 (8H, broad s);
2.93 (4H, m);
1.3 (3H, t, J=7 Hz);
1.2 (3H, t, J=7 Hz).

(k)
4-(Diethyl-1-methyl-4-[2-(3-thienyl)-ethyl]-pyrrole-2-acetate-3-carboxylate-5-carboxylic acid)-morpholide

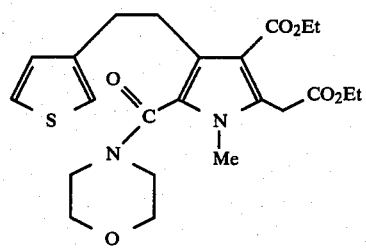

This compound was prepared in an analogous manner to the preparation of ethyl 5-N,N-dimethylcarboxamido-4-[2-(3-thienyl)-ethyl]-3-ethoxycarbonyl-1-methylpyrrole-2-acetate (Example 1(c)), as an oil (yield 93%) but using dry dioxane in place of isobutyl methylketone.
N.M.R. δ (CDCl₃):
  7.12 (1H, m);
  6.88 (2H, m);
  4.3 (2H, q, J=7 Hz);
  4.2 (2H, q, J=7 Hz);
  4.06 (2H, s);
  3.67 (8H, broad s);
  3.45 (3H, s);
  2.85 (4H, broad s);
  1.3 (3H, t, J=7 Hz);
  1.23 (3H, t, J=7 Hz).

(1d) Diethyl 4,5-dihydro-8-methyl-9-oxo-9H-thieno[3',2':5,6]cyclohepta[1,2-b]pyrrole-7-acetate-6-carboxylate

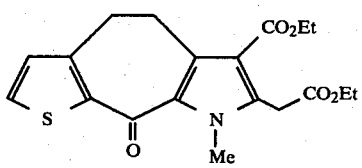

Subsequent cyclization in phosphoryl chloride as in Example 1(d), of the product of (k) above, was complete in 3 hours affording a solid product, yield 56%, m.p. 103°-106°. Recrystallisation from ether/petroleum ether 60°-80° gave white fine needles m.p. 115°-116°, having the same NMR as given above.

EXAMPLE 2

(2a)
4-(Dimethyl-4-[2-(3-thienyl)-ethyl]-pyrrole-2-(3'-propanoate)-3-carboxylate-5-carboxylic acid)-morpholide

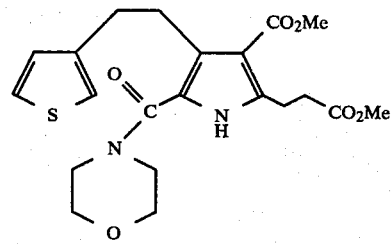

Sodium nitrite (24.0 g, 0.35 mole) in water (40.0 ml) was added dropwise with stirring to a solution of the morpholide from Example 1(i) (90.5 g, 0.39 mole) in glacial acetic acid (500 ml) between 5° and 7°. After completing the addition, the mixture was stirred for 3 hours at room temperature and then left to stand overnight in the 'fridge. The resulting solution was added slowly to a solution of dimethyl 3-oxo adipate (72.6 g, 0.39 mole) in glacial acetic acid (1100 ml) at 70° with concurrent addition of a mixture of zinc powder (111.7 g, 1.7 mole) in anhydrous sodium acetate (139.5 g, 1.7 mole) so that the temperature was kept at about 80°. After these additions, the mixture was stirred at reflux temperature for 1 hour before pouring into cold water (10 l). The mixture was extracted into methylene chloride (6×500 ml), the organic layers were combined, washed with dilute sodium bicarbonate solution until pH 7, dried (anhydrous MgSO₄), filtered and the solvents removed on a rotary evaporator to afford an oil. The product was purified on a silica gel column eluting with ethyl acetate to give an oil 76.4 g (45%). A small quantity of the oil was induced to crystallise. Recrystallisation from ether/pentane gave a white solid m.p. 105°-106°.
N.M.R. δ (CDCl₃):
  10.0 (1H, broad s);
  7.18 (1H, m);
  6.85 (2H, m);
  3.78 (3H, s);
  3.6 (11H, m);
  3.32-2.44 (8H, symmetrical m).

(b) 3-(Methyl 5-N,N-dimethylcarboxamido-4-[2-(3-thienyl)-ethyl]-3-methyoxycarbonyl-pyrryl-2-)propanoate

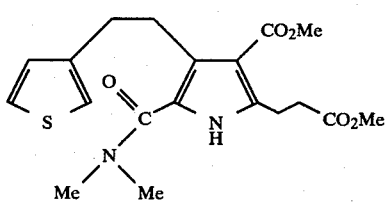

This compound was prepared in an analogous manner to Example 2(a) but using the compound prepared in Example 1(a) in place of the morpholide. A white crystalline solid was obtained after recrystallisation from ethyl acetate/ether (yield 40%) m.p. 128°-129°.

N.M.R. δ (CDCl₃):
  10.05 (1H, broad s);
  7.14 (1H, m);
  6.9 (2H, m);
  3.8 (3H, s);
  3.61 (3H, s);
  3.34–2.4 (14H, m).

(c) 4-(Dimethyl-4-[2-(3-thienyl)-ethyl]-1-methylpyrrole-2-(3'-propanoate)-3-carboxylate-5-carboxylic acid)-morpholide

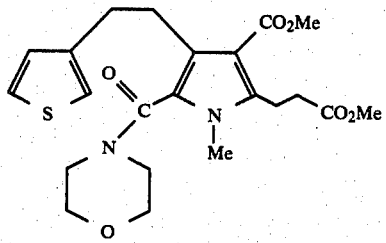

The NH compound, Example 2(a), (68.4 g, 0.16 mole) was dissolved in dry dioxane (250 ml) and added to a suspension of 50% sodium hydride (7.68 g, 0.16 mole) in dry dioxane (250 ml), under an atmosphere of nitrogen. Dimethyl sulphate (10.08 g, 0.08 mole) was added to the magnetically stirred mixture and the reaction brought to reflux temperature for 6 hours. The reaction was then cooled, poured into cold dilute hydrochloric acid and the aqueous mixture extracted into ethyl acetate. The organic extracts were combined, washed with water, dried (anhydrous MgSO₄), filtered and evaporated to give an oil.

The product was purified on a silica gel column eluting with 1% methanol/CHCl₃ to afford a white solid (60 g, 84%) m.p. 116°–117°.
N.M.R. δ (CDCl₃):
  7.13 (1H, m);
  6.85 (2H, m);
  3.9–2.33 (25H, m with s at 3.73, 3.6 and 3.48)

(d) 3-(Methyl 5-N,N-dimethylcarboxamido-4-[2-(3-thienyl)-ethyl]-3-methoxycarbonyl-1-methylpyrryl-2-)propanoate

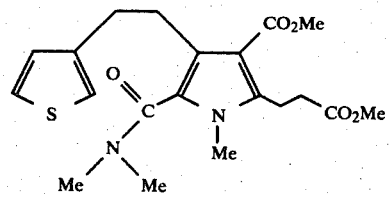

This compound was prepared from Example 2(b) in an analogous manner to Example 2(c).
N.M.R. δ (CDCl₃):
  7.21 (1H, m);
  6.9 (2H, m);
  3.8 (3H, s);
  3.67 (3H, s);
  3.5 (3H, s);
  3.48–2.4 (14H, m).

(e) 3-(Dimethyl 4,5-dihydro-8-methyl-9-oxo-9H-thieno[3',2':5,6]cyclohepta[1,2-b]pyrryl-6-carboxylate-7-)propanoate

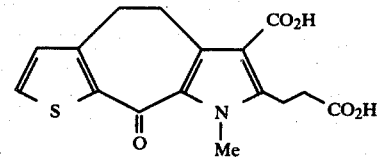

The NMe pyrrole (60 g, 0.134 mole) from Example 2(c) was dissolved in phosphoryl chloride (350 ml), under an atmosphere of nitrogen and the stirred mixture refluxed for 6 hours. After cooling the reaction was poured carefully onto ice covered with ethyl acetate. Neutralization of the aqueous solution was achieved by the addition of solid sodium carbonate. The organic layer was separated and the aqueous layer re-extracted with ethyl acetate. The combined organic layers were washed with saturated sodium chloride solution, water, dried (anhydrous MgSO₄), filtered and evaporated to give a black oil. Purification by column chromatography, eluting with ethyl acetate on silica gel, afforded the product as a white solid (29.0 g, 60%) m.p. 136°–137°.
N.M.R. δ (CDCl₃):
  7.53 (1H, d, J=5 Hz);
  6.98 (1H, d, J=5 Hz);
  3.98 (3H, s);
  3.88 (3H, s);
  3.72 (3H, s);
  3.56–2.43 (8H, m).

The above compound was also prepared from Example 2(d) in a similar way to give the required product in 21% yield.

(f) 3-(4,5-Dihydro-8-methyl-9-oxo-9H-thieno[3',2':5,6]cyclohepta[1,2-b]pyrryl-6-carboxylic acid-7-)propanoic acid 20 g (0.055 mole) of the diester, (Example 2(e)), was refluxed in 25% aqueous sodium hydroxide (75 ml) and methanol (20 ml) for 2 hours. The solution was then cooled, the methanol removed on the rotary evaporator and the residue poured into water. The aqueous solution was washed with ethyl acetate and acidified with dilute hydrochloric acid. The resulting yellow precipitate was filtered off and dried at the pump to give the product (18 g, 98%) m.p. 215°–216°.

(g)
3-(4,5-Dihydro-8-methyl-9-oxo-9H-thieno[3',2':5,6]cyclohepta[1,2-b]pyrryl-7-)propanoic acid

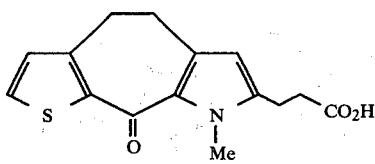

The diacid (17.0 g, 0.051 mole, Example 2(f)) was heated under nitrogen at 220° in an oil bath for 2½ hours. The crude product was recrystallised from CHCl₃ to give a white solid (11 g, 75%) m.p. 178°-180°.
N.M.R. δ (d₆-DMSO):
 7.5 (1H, d, J=5 Hz);
 6.9 (1H, d, J=5 Hz);
 5.82 (1H, s);
 4.7 (1H, broad s);
 3.82 (3H, s);
 3.07-2.4 (8H, m with broad s at 2.87).

(h)
4-(4,5-Dihydro-8-methyl-9-oxo-9H-thieno[3',3':5,6]cyclohepta[1,2-b]pyrryl-7-)butan-2-one

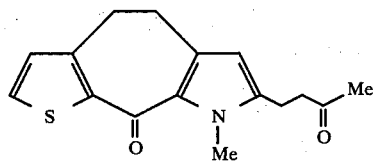

The propanoic acid (10 g, 0.0346 mole, Example 2(g)) was dissolved in dry tetrahydrofuran (100 ml) together with dry triethylamine (6.1 ml, 0.045 mole) under nitrogen and the mixture cooled to −20°. Ethyl chloroformate (4.1 ml, 0.044 mole) was added dropwise and the solution at −20° until a precipitate began to form. The reaction was then left to stand in the freezer (−20°) overnight. The precipitate was then filtered off and the filtrate added, whilst cold, to a solution prepared by the treatment of bis (trimethylsilyl) malonate (16.5 g, 0.073 mole) in dry ether (250 ml) under nitrogen at −70° with a solution of n-butyllithium in hexane (56 ml, 1.15 M; 0.071 mole) warmed to −15°. The resulting solution was stirred at −15° for 30 minutes before quenching the reaction by addition of 5% aqueous sodium bicarbonate (250 ml). The aqueous layer was separated and the organic layer further extracted with sodium bicarbonate solution (1×100 ml) before combining the aqueous layers and acidifying with dilute hydrochloric acid. The acidic solution was extracted with ethyl acetate (2×250 ml), the orgaic layers then combined and washed with water (2×100 ml) and evaporated to dryness to give a solid. This was heated in dimethyl sulphoxide (100 ml) containing water (10 ml) at 100° for 30 minutes. The solution was poured into excess 5% aqueous sodium bicarbonate and the resulting mixture extracted with ethyl acetate (2×250 ml). The organic layers were combined, washed with water (2×100 ml), dried (anhydrous MgSO₄) and concentrated to give a yellow solid. This was purified on a silica gel column eluting with ether to give the product as pale yellow needles (6 g, 60%) m.p. 115°-116° (after recrystallisation from ether/pentane).
N.M.R. δ (CDCl₃):
 7.45 (1H, d, J=5 Hz);
 6.93 (1H, d, J=5 Hz);
 5.81 (1H, s);
 3.93 (3H, s);
 2.93 (4H, broad s);
 2.83 (4H, s);
 2.19 (3H, s).

EXAMPLE 3

4-(4,5-Dihydro-8-methyl-9-oxo-9H-thieno[3',2':5,6]cyclohepta[1,2-b]pyrryl)-7-)butan-2-ol

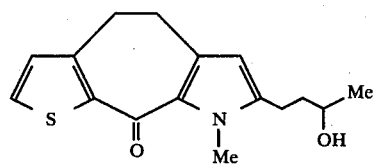

A mixture of the butanone (200 mg, 0.0007 mole, Example 2(h)) and sodium borohydride (34 mg, 0.0009 mole) was stirred for 40 minutes in ethanol at room temperature. After the addition of saturated aqueous ammonium chloride solution (10 ml) the mixture was concentrated and the residue partitioned between chloroform (25 ml) and water (25 ml). The chloroform layer was washed with water (15 ml), dried (Na₂SO₄), filtered and the solvent evaporated to give a solid.
N.M.R. δ (CDCl₃):
 7.3 (1H, d, J=5 Hz);
 6.78 (1H, d, J=5 Hz);
 5.65 (1H, s);
 3.93-3.4 (4H, m with s at 3.79);
 3.02-2.45 (6H, m with broad s at 2.85);
 2.26 (1H, s);
 1.88-1.48 (2H, m);
 1.19 (3H, d, J=6 Hz).

EXAMPLE 4

2-Acetoxy-4-(4,5-dihydro-8-methyl-9-oxo-9H-thieno[3',2':5,6]cyclohepta[1,2-b]pyrryl-7-)butane

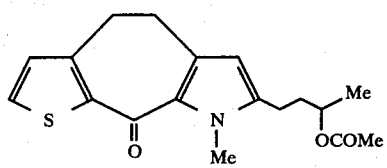

The above product (Example 3) was dissolved in a solution of dry toluene (30 ml) and dry pyridine (0.4 ml). The reaction mixture was cooled to 0°, acetyl chloride (0.1 ml, 0.0014 mole) added and then stirred at room temperature for 1 hour. The solution was treated with cold water (30 ml) before being extracted with ether (2×40 ml). The organic layer was washed with water, 1 N HCl, water again, dried (anhydrous MgSO₄), filtered and the solvent evaporated to give a yellow solid. Purification on a short silica gel column eluting with ether afforded the product as a white solid (100 mg, 43% from the butanone) m.p. 96°-98° (after recrystallisation from ether/pentane).
N.M.R. δ (CDCl₃):

7.28 (1H, d, J=5 Hz);
6.63 (1H, d, J=5 Hz);
5.65 (1H, s);
5.02–4.67 (1H, m);
3.81 (3H, s);
2.85 (4H, broad s);
2.77–2.3 (2H, m);
2.08–1.6 (5H, m with s at 1.98)
1.23 (3H, d, J=6 Hz).

EXAMPLE 5

5(a) Diethyl 8-methyl-9-oxo-9H-thieno[3',2':5,6]cyclohepta[1,2-b]pyrrole-7-acetate-6-carboxylate

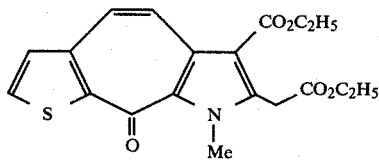

The di-ester from Example 1(d) (0.375 g, 0.001 mole) was dissolved in dry carbon tetrachloride (30 ml), N-bromosuccinimide (0.178 g, 0.001 mole) added and the mixture refluxed for 2 hours. The reaction was allowed to cool and then left to stand at room temperature overnight. The precipitate was filtered off, the solvent removed from the filtrate and the resulting solid dissolved in a small volume of chloroform and diluted with excess ether to give a crystalline precipitate (0.22 g, 59%).
N.M.R. δ (CDCl$_3$):
  8.44 (1H, d, J=12 Hz);
  7.68 (1H, d, J=5 Hz);
  7.32 (1H, d, J=5 Hz);
  7.31 (1H, d, J=12 Hz);
  4.38 (2H, q, J=7 Hz);
  4.29 (3H, s);
  4.25 (2H, s);
  4.17 (2H, q, J=7 Hz);
  1.41 (3H, t, J=7 Hz);
  1.27 (3H, t, J=7 Hz);

(b) 8-Methyl-9-oxo-9H-thieno[3',2':5,6]cyclohepta[1,2-b]pyrrole-7-acetic acid-6-carboxylic acid

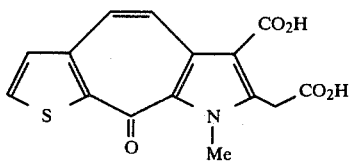

The dehydro diester from Example 5(a) (0.98 g, 0.0026 mole) was refluxed for 2 hours with 25% aqueous sodium hydroxide (20 ml) and ethanol (5 ml). After cooling the solution was diluted with water (30 ml), washed with ether (2×50 ml), acidified with dilute hydrochloric acid and the solid precipitate filtered off and dried to give the diacid (0.64 g, 83%).
N.M.R. δ (d$_6$-DMSO) (wet)
  8.45 (1H, d, J=12 Hz);
  8.05 (1H, d, J=5 Hz);
  7.51 (1H, d, J=5 Hz);
  7.48 (1H, d, J=12 Hz);
  4.74 (broad);
  4.34 (2H, s);
  4.2 (3H, s).

(c) Ethyl 8-methyl-9-oxo-9H-thieno[3',2':5,6]-cyclohepta[1,2-b]pyrrole-7-acetate-6-carboxylic acid

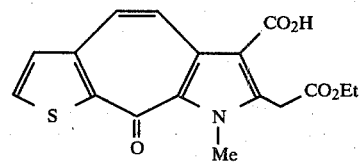

A suspension of the crude diacid from Example 5(b) (0.64 g, 0.002 moles) in 0.7% HCl in ethanol (10.3 ml) was refluxed for 1¼ hours. The solid slowly dissolved and reprecipitated as the monoester on cooling. The product was filtered off, washed with a small volume of cold ethanol and ether to afford a crystalline product (0.62 g, 70%) m.p. 276°–280°.
N.M.R. δ (d$_6$-DMSO/D$_2$O)
  8.57 (1H, d, J=12 Hz);
  8.18 (1H, d, J=5 Hz);
  7.68 (1H, d, J=5 Hz);
  7.60 (1H, d, J=12 Hz);
  4.55–3.5 (complex);
  1.36 (3H, t, J=7 Hz).

(d) Ethyl 8-methyl-9-oxo-9H-thieno[3',2':5,6]-cyclohepta[1,2-b]pyrrole-7-acetate

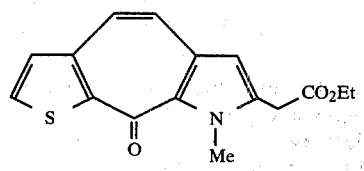

The monoester from Example 5(c) (0.32 g, 0.00093 mole) was heated in dry quinoline (4 ml) at 190° with dried copper bronze for 30 minutes under dry nitrogen. The reaction was then cooled, the copper filtered off through Kieselguhr and rinsed with ethyl acetate and water. The filtrate was acidified with dilute hydrochloric acid (25 ml) and extracted with ethyl acetate (75 ml). The organic layer was washed with dilute hydrochloric acid (25 ml), aqueous sodium carbonate (2×25 ml), saturated sodium chloride solution (30 ml), dried (MgSO$_4$), filtered and evaporated to give a gum (0.25 g). Purification by column chromatography on silica gel eluting with 1:1 petroleum ether 60°–80°: ether afforded the product as an orange oil (0.14 g, 50%).
N.M.R. δ (CCl$_4$):
  7.5 (1H, d, J=5 Hz);
  7.13 (1H, d, J=5 Hz);
  7.02 (2H, s);
  6.3 (1H, s);
  4.18 (3H, s);
  4.1 (2H, t, J=7 Hz);
  3.62 (2H, s);
  1.23 (3H, t, J=7 Hz).

(e) 8-Methyl-9-oxo-9H-thieno[3',2':5,6]-cyclohepta[1,2-b]pyrrole-7-acetic acid

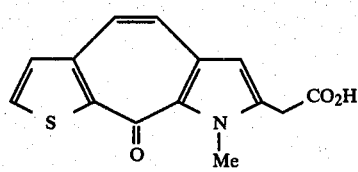

The ethyl ester from Example 5(d) (0.14 g, 0.00047 mole) was refluxed in ethanol (1.5 ml) and 5% aqueous sodium hydroxide (10 ml) for 1½ hours. The reaction was then poured into water (50 ml), extracted with ethyl acetate (2×50 ml) and the aqueous layer acidified with dilute hydrochloric acid. The cloudy solution was extracted into ethyl acetate (2×50 ml), the organic layers combined, washed with water (2×50 ml), dried (MgSO₄), filtered and evaporated to give a yellow solid. The solid was suspended in ether and filtered off to give the product (0.096 g, 75%) m.p. 185°–8°.

Mass Spectrum: m/e 273.0471 observed, m/e 273.0459 calculated ($C_{14}H_{11}NO_3S$).

EXAMPLE 6

Sodium 4,5-dihydro-8-methyl-9-oxo-9H-thieno[3',2':5,6]cyclohepta[1,2-b]pyrrole-7-acetate

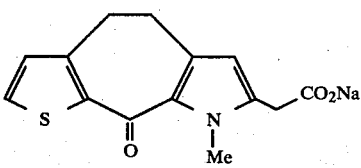

The tricyclic acetic acid from Example 1(h) (0.5 g, 0.0018 mole) was dissolved in ethanol (15 ml) and ethanolic sodium hydroxide (0.072 g, 0.0018 mole) added. The resulting precipitate was filtered off, rinsed with ethanol and ether to give a white solid (0.474 g, 88%), m.p. 275°–278° (darkens).

EXAMPLE 7

(a) 2-(4,5-Dihydro-8-methyl-9-oxo-9H-thieno[3',2':5,6]cyclohepta[1,2-b]pyrryl-7-)propanoic acid

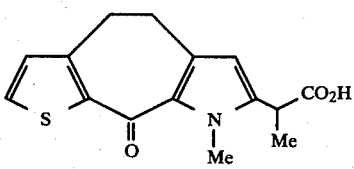

To diisopropylamine (0.76 ml, 0.0054 mole) in dry tetrahydrofuran under an atmosphere of nitrogen was added n-butyllithium (4.75 ml; 1.15 M in hexane) at −78°. The acetic acid (0.75 g, 0.0027 mole, Example 1(h)) in dry tetrahydrofuran was then added to give a deep purple mixture. After stirring at −78° for 15 minutes methyl iodide (0.17 ml, 0.0027 mole) was introduced and the reaction warmed to room temperature. Two further additions of methyl iodide (2×0.17 ml) at 2½ hour intervals followed by overnight stirring gave a clear orange solution containing a yellow precipitate. The reaction was quenched with dilute hydrochloride acid and the product extracted into ethyl acetate.

The organic layer was then extracted with dilute sodium hydroxide solution and the aqueous layer washed with ethyl acetate. The product was isolated by acidification of the basic solution, extraction with ethylacetate and the organic layer washed with water, dried (anhydrous MgSO₄), filtered and the solvent removed in vacuo to give a solid. Recrystallisation from chloroform/pentane afforded the required product, mp 155°–7°.

NMR δ (CDCl₃):
9.5 (1H, broad s);
7.39 (1H, d, J=5 Hz);
6.85 (1H, d, J=5 Hz);
5.98 (1H, s);
3.9 (3H, s);
3.8 (1H, q, J=7 Hz);
2.93 (4H, broad s);
1.58 (3H, d, J=7 Hz).

The acid was also prepared from its ethyl ester (Example 7(b)) by hydrolysis with 5% sodium hydroxide solution in a similar manner to Example 1(h) to give bright yellow crystals, mp 156°–7°.

(b) Ethyl 2-(4,5-dihydro-8-methyl-9-oxo-9H-thieno[3',2':5,6]cyclohepta[1,2-b]pyrryl-7-)propanoate

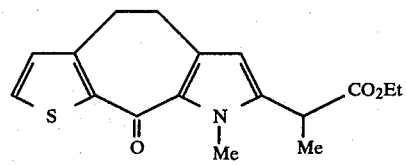

The above propionic acid was esterified by refluxing the compound in ethanolic hydrochloric acid (0.5%) for 3 hours. The solution was then concentrated and partitioned between the ether and water. The ether layer was washed with dilute sodium hydroxide, water, dried (over anhydrous Na₂SO₄), filtered and evaporated to give an oil. The product was purified on a silica gel column eluting with ether:petroleum ether (60°–80°) (1:4).

Nmr δ (CCl₄):
7.23 (1H, d, J=5 Hz);
6.7 (1H, d, J=5 Hz);
5.75 (1H, s);
4.01 (2H, q, J=7 Hz);
3.81 (3H, s);
3.63 (1H, q, J=7 Hz);
2.84 (4H, broad s);
1.42 (3H, d, J=7 Hz);
1.18 (3H, t, J=7 Hz).

EXAMPLE 8

(a) Ethyl 3-oxo-5-(2-thienyl)-pentanoate

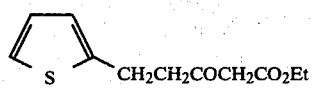

Ethyl acetoacetate (15.6 g, 0.12 mole) in dry tetrahydrofuran (300 ml) was added to a suspension of sodium hydride (80%) (4.0 g, 0.13 mole) in dry tetrahydrofuran (30 ml), under nitrogen with mechanical stirring and the reaction kept at 0°. n-Butyl lithium (125 ml, 1.15 M in hexane) was then added dropwise whilst the temperature was maintained between −5° and 0°. To the resulting dianion mixture was added 2-chloromethyl thiophene (25.0 g, 0.18 mole) in dry ether, dropwise and at 0°. The reaction was then allowed to warm up to room temperature and stirring was continued for 1 hour before placing the mixture in the 'fridge overnight. The reaction was worked up as in Example 1(i) to give a crude oil. Unreacted ethylacetoacetate and 2-chloromethylthiophene were removed by vacuum distillation and the required crude product obtained as the residue (23 g, 84%).

Nmr δ (CCl₄):
7.2–6.7 (3H, complex);
4.28–3.82 (2H, q, J=7 Hz);
3.22 (2H, s);
3.22–2.58 (4H, m);
1.25 (3H, t, J=7 Hz).

(b) Benzyl 3-oxo-5-(2-thienyl)-pentanoate

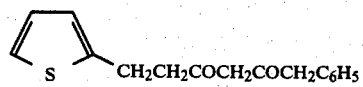

The crude ethyl ester was heated together with dry distilled benzyl alcohol (8.0 g, 0.074 mole) at 120° (oil bath temperature) with nitrogen passing through the mixture, until no more ethanol distilled off. The excess benzyl alcohol was removed by distillation under reduced pressure to leave the crude product as an oil (25 g).

Nmr δ (CCl₄):
7.28 (5H, s);
7.10–6.58 (3H, m);
5.01 (2H, s);
3.28 (2H, s);
3.2–2.55 (4H, m).

(c) Ethyl 5-benzyloxycarbonyl-3-ethoxycarbonyl-4-[2-(2-thienyl)-ethyl]-pyrrole-2-acetate

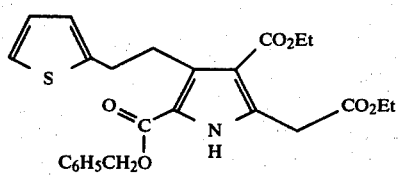

This compound was prepared in an analogous manner to the preparation of ethyl 5-N,N-dimethyl carboxamido-3-ethoxycarbonyl-4-[2-(3-thienyl)-ethyl]-pyrrole-2-acetate (Example 1(b)), as a pale yellow solid (yield 31%), mp 105°–8°.

Nmr δ (CDCl₃):
10.32 (1H, broad s);
7.35 (5H, s);
7.6–6.55 (3H, complex set of m);
5.3 (2H, s);
4.29 (2H, q, J=7 Hz);
4.18 (2H, q, J=7 Hz);
4.03 (2H, s);
3.6–2.8 (4H, sym m);
1.32 (3H, t, J=7 Hz);
1.25 (3H, t, J=7 Hz).

(d) Ethyl 5-benzyloxy-carbonyl-3-ethoxycarbonyl-1-methyl-4-[2-(2-thienyl)-ethyl]-pyrrole-2-acetate

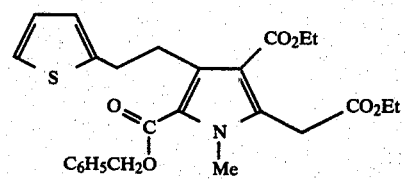

N-Methylation of the above 2-thienyl substituted pyrrole was achieved in an analogous manner to that described in Example 2(c) to give the product as white needles (yield 60%), mp 81°–84°.

Nmr δ (CDCl₃):
7.31 (5H, s);
7.6–6.46 (3H, complex set of m);
5.28 (2H, s);
4.23 (2H, q, J=7 Hz);
4.14 (2H, q, J=7 Hz);
4.08 (2H, s);
3.78 (3H, s);
3.57–2.7 (4H, sym m);
1.3 (3H, t, J=7 Hz);
1.24 (3H, t, J=7 Hz).

(e) Ethyl 3-ethoxycarbonyl-1-methyl-4-[2-(2-thienyl)-ethyl]-pyrrole-2-acetate-5-carboxylic acid

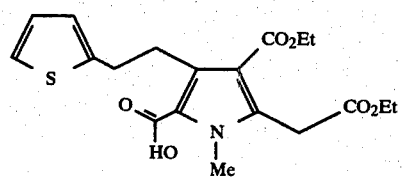

The above benzyl ester (2.74 g) was dissolved in dry xylene (200 ml) under an atmosphere of nitrogen and 10% Pd/C (2 g) suspended in ethanol (20 ml) added, followed by cyclohexene (100 ml). The mixture was stirred and heated at reflux temperature until all the starting material had debenzylated (tlc silica gel eluted with chloroform/methanol 9:1). After cooling the reaction was filtered through Kieselguhr and the solvents removed in vacuo. The residue was taken up into ethyl acetate and then extracted into dilute sodium carbonate. The aqueous layer was washed with ethyl acetate, acidified with dilute hydrochloric acid and extracted with chloroform. The chloroform layer was washed with water, dried (anhydrous Na₂SO₄) filtered and evaporated to give the product as a white solid, mp 115°–118°.

Nmr δ (CDCl₃):
9.33–8.63 (1H, broad s);
7.61–6.73 (3H, m);
4.22 (2H, q, J=7 Hz);
4.1 (2H, q, J=7 Hz);
4.08 (2H, s);
3.79 (3H, s);

3.54–2.86 (4H, sym m);
1.32 (3H, t, J=7 Hz);
1.2 (3H, t, J=7 Hz).

This reaction was repeated twice in analogous manner but using (1) ethanol as solvent instead of dry xylene; (2) methanol as solvent instead of the dry xylene, and sodium formate at room temperature instead of cyclohexene.

(f) Diethyl 8,9-dihydro-5-methyl-4-oxo-4H-thieno[2',3':5,6]cyclohepta[1,2-b]pyrrole-6-acetate-7-carboxylate

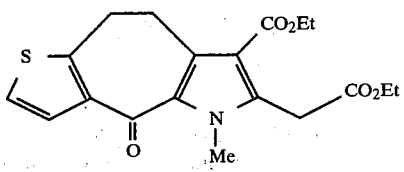

The above acid (0.4 g) was dissolved in benzene (50 ml) and thionyl chloride (1 ml) added dropwise. The reaction was refluxed for 1 hour, cooled and the solvent removed in vacuo. The residue was dissolved in dry benzene and the solvent again removed in vacuo to ensure the removal of any excess thionyl chloride. The resulting oil was dissolved in dry benzene (50 ml) and cooled to 5° in an ice bath. Stannic chloride (1 ml) in dry benzene (5 ml) was added dropwise and the mixture stirred at 5° for 10 minutes. After allowing the reaction to warm to room temperature the mixture was warmed at 70° on a steam bath for 15 minutes before being cooled again to 5° and quenched with dilute hydrochloric acid in the presence of ether (50 ml). The organic layer was separated off and washed with saturated sodium chloride solution, 10% sodium carbonate solution and saturated sodium chloride solution once again. After drying (anhydrous MgSO₄), filtering and evaporating the residue was purified on a silica gel column eluting with ether to give the required product as white needles, mp 123°–124° (0.3 g, 79%).

Nmr δ(CCl₄):
7.41 (1H, d, J=5 Hz);
6.72 (1H, d, J=5 Hz);
4.14 (2H, q, J=7 Hz);
4.02 (2H, q, J=7 Hz);
3.9 (2H, s);
3.79 (3H, s);
3.6–2.84 (4H, sym m);
1.3 (3H, t, J=7 Hz);
1.2 (3H, t, J=7 Hz).

(g) 8,9-Dihydro-5-methyl-4-oxo-4H-thieno[2',3':5,6]cyclohepta[1,2-b]pyrrole-6-acetic acid-7-carboxylic acid

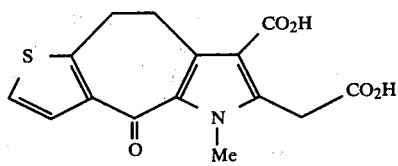

This compound was prepared from the above compound, Example 8(f), in an analogous manner to the preparation of Example 1(e).

Nmr δ(CDCl₃/(CD₃)₂CO/D₂O):
7.52 (1H, d, J=5 Hz);
6.98 (1H, d, J=5 Hz);
4.23 (2H, s);
3.99 (3H, s);
3.74–2.95 (4H, sym m).

(h) Ethyl 8,9-dihydro-5-methyl-4-oxo-4H-thieno[2',3':5,6]cyclohepta[1,2-b]pyrrole-6-acetate-7-carboxylic acid

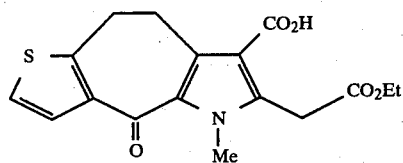

This compound was prepared from Example 8(g) in an analogous manner to the preparation of Example 1(f).

Nmr δ(CDCl₃):
9.8 (1H, s);
7.56 (1H, d, J=5 Hz);
6.88 (1H, d, J=5 Hz);
4.15 (2H, s);
4.14 (2H, q, J=7 Hz);
3.88 (3H, s);
3.63–2.93 (4H, sym m);
1.28 (3H, t, J=7 Hz).

(i) Ethyl 8,9-dihydro-5-methyl-4-oxo-4H-thieno[2',3':5,6]cyclohepta[1,2-b]pyrrole-6-acetate

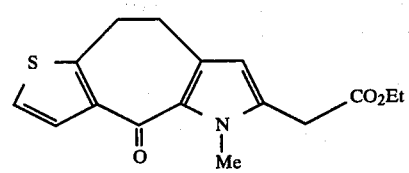

This compound was prepared from Example 8(h) in an analogous manner to the preparation of Example 1(g).

Nmr δ(CCl₄):
7.49 (1H, d, J=5 Hz);
6.78 (1H, d, J=5 Hz);
5.78 (1H, s);
4.1 (2H, q, J=7 Hz)
3.88 (3H, s);
3.5 (2H, s);
3.2–2.72 (4H, m);
1.27 (3H, t, J=7 Hz).

(j) 8,9-Dihydro-5-methyl-4-oxo-4H-thieno[2',3':5,6]cyclohepta[1,2-b]pyrrole-6-acetic acid

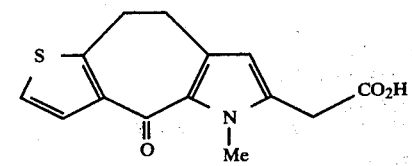

This compound was prepared from Example 8(i) in an analogous manner to the preparation of Example 1(h).
Nmr δ(CDCl$_3$):
8.34 (1H, broad s);
7.6 (1H, d, J=5 Hz);
6.88 (1H, d, J=5 Hz);
5.93 (1H, s);
3.92 (3H, s);
3.67 (2H, s);
3.26–2.68 (4H, m).

PHARMACOLOGICAL DATA SECTION

1. Analgesic Activity

The compounds of this invention were examined for analgesic activity in the conventional Phenyl Quinone Writhing Test.

The compound of Example 1(h) was active in this test at 0.5 mg/kg p.o.

The compound of Example 2(h) was active in this test at 8.0 mg/kg p.o.

The compound of Example 5(e) was active in this test at 32 mg/kg p.o.

The compound of Example 6 was active in this test at 1.0 mg/kg p.o.

2. Anti-Inflammatory Activity

The compounds of this invention were examined for anti-inflammatory activity in the conventional Carrageenin Induced Oedema Test.

The compound of Example 1(h) was active in this test at 0.5 mg/kg p.o.

The compound of Example 2(h) was active in this test at 12.5 mg/kg p.o.

The compound of Example 6 was active in this test at 0.5 mg/kg p.o.

3. Toxicity

No toxic effects were observed in any of the above tests.

We claim:

1. A compound of the formula (I):

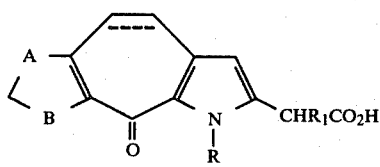

wherein
R is C$_{1-4}$ alkyl;
R$_1$ is hydrogen or C$_{1-4}$ alkyl;
one of A and B is sulphur and the other of A and B is carbon doubly bound to the carbon spacing A and B; and the dotted line represents an optionally present double bond; and pharmaceutically acceptable salts of the compounds of formula (I) and in vivo hydrolyzable esters of said compounds selected from the group consisting of the C$_1$–C$_4$ alkyl, unsubstituted or substituted by hydroxy or methoxy, benzyl, lower-acyloxymethyl, α-loweracyloxyethyl, loweralkoxycarbonyloxymethyl, α-loweralkoxycarbonyloxyethyl and phthalidyl, and in vivo hydrolyzable amides of said compounds selected from the group consisting of primary amide, loweralkylamide and (di-loweralkyl) amide.

2. A compound according to claim 1, of the formula (II):

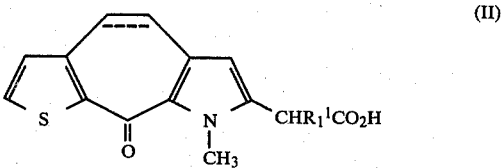

and pharmaceutically acceptable salts and said in vivo hydrolyzable esters and amides thereof;
wherein R$_1$$^1$ is hydrogen or methyl.

3. A compound according to claim 2, wherein the dotted line does not represent a further bond.

4. 4,5-Dihydro-8-methyl-9-oxo-9H-thieno[3',2':5,6]cyclohepta[1,2-b]pyrrole-7-acetic acid.

5. Sodium 4,5-dihydro-8-methyl-9-oxo-9H-thieno[3',2':5,6]cyclohepta[1,2-b]pyrrole-7-acetate.

6. A compound according to claim 1 of the formula (III):

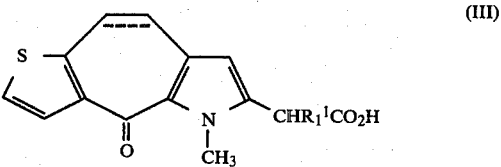

and pharmaceutically acceptable salts and in vivo hydrolyzable esters and amides thereof;
wherein R$^1$ is hydrogen or methyl and the dotted line is as defined in claim 1.

7. An anti-inflammatory and/or analgesic pharmaceutical composition, which comprises an anti-inflammatory and/or analgesic effective amount of a compound according to claim 1, and a pharmaceutically acceptable carrier.

8. A method of treatment of inflammation or painful conditions in mammals, which comprises administering to the sufferer an effective amount of a compound according to claim 1.

* * * * *